US008854208B2

(12) United States Patent
Huizenga et al.

(10) Patent No.: US 8,854,208 B2
(45) Date of Patent: Oct. 7, 2014

(54) WIRELESS SENSOR

(75) Inventors: Charles Huizenga, Berkeley, CA (US); Michael Corr, San Francisco, CA (US)

(73) Assignee: ABL IP Holding LLC, Atlanta, GA (US)

(*) Notice: Subject to any disclaimer, the term of this patent is extended or adjusted under 35 U.S.C. 154(b) by 0 days.

(21) Appl. No.: 12/940,902

(22) Filed: Nov. 5, 2010

(65) Prior Publication Data

US 2011/0109424 A1    May 12, 2011

Related U.S. Application Data

(60) Provisional application No. 61/258,845, filed on Nov. 6, 2009, provisional application No. 61/258,841, filed on Nov. 6, 2009.

(51) Int. Cl.
*G08B 1/08* (2006.01)
*G08B 13/08* (2006.01)
*G05B 15/02* (2006.01)

(52) U.S. Cl.
CPC ..................................... *G05B 15/02* (2013.01)
USPC ..... 340/539.26; 340/3.1; 340/541; 340/545.4

(58) Field of Classification Search
CPC ............... G09G 2320/0261; G09G 2320/106; G09G 2320/0252; G09G 2340/16; G09G 2340/0435; G09G 2320/103; G09G 2320/0276; G09G 2320/0285; G09G 2360/18; G06Q 30/00; H04N 5/145; G06F 17/30539; G06F 21/60; G06F 3/017; G06K 9/00369; G06K 9/00771; G05B 15/02; G05B 23/02
USPC .......... 340/3.1, 541, 13.24, 567, 531, 539.26, 340/691.3, 3.5; 370/438; 455/345, 457; 315/149; 239/63
See application file for complete search history.

(56) References Cited

U.S. PATENT DOCUMENTS

| | | | |
|---|---|---|---|
| 3,733,528 A | 5/1973 | Gilbreath | |
| 3,735,141 A | 5/1973 | Beling | |
| 4,242,614 A | 12/1980 | Vatis et al. | |
| 4,323,820 A | 4/1982 | Teich | |
| 4,347,461 A | 8/1982 | Carlson | |
| 4,355,309 A | 10/1982 | Hughey et al. | |
| 4,358,717 A | 11/1982 | Elliott | |
| 4,388,567 A | 6/1983 | Yamazaki et al. | |
| 4,454,509 A | 6/1984 | Buennagel et al. | |

(Continued)

OTHER PUBLICATIONS

Adams, J.T., "Wireless Sensors and Controls Make the Organic Building," May 2006, Proceedings of the 2006 IEEE Intl. Symposium on Electronics and the Environment, pp. 109-113.

(Continued)

*Primary Examiner* — Omer S Khan
(74) *Attorney, Agent, or Firm* — Carr & Ferrell LLP (57) ABSTRACT

Systems and methods for wirelessly detecting area changes are provided. Predetermined thresholds may be stored in memory. Each predetermined threshold is associated with a time of day, calendar day, and/or activity. The sensor may detect a change in the in the targeted area. The detected change is evaluated to determine an applicable threshold. Then it may be determined whether the detected change meets a predetermined threshold. If so, information regarding the change is wirelessly transmitted to an associated controller that controls light in the targeted area. The operation of the light may be controlled based on the wirelessly transmitted information.

13 Claims, 2 Drawing Sheets

(56) References Cited

U.S. PATENT DOCUMENTS

| | | | |
|---|---|---|---|
| 4,686,380 A | | 8/1987 | Angott |
| 4,797,599 A | | 1/1989 | Ference et al. |
| 4,889,999 A | | 12/1989 | Rowen |
| 5,005,211 A | | 4/1991 | Yuhasz |
| 5,146,153 A | | 9/1992 | Luchaco et al. |
| 5,237,264 A | | 8/1993 | Moeley et al. |
| 5,248,919 A | | 9/1993 | Hanna et al. |
| 5,268,631 A | | 12/1993 | Gorman et al. |
| 5,357,170 A | | 10/1994 | Luchaco et al. |
| 5,373,453 A | | 12/1994 | Bae |
| 5,471,063 A | | 11/1995 | Hayes et al. |
| 5,561,351 A | | 10/1996 | Vrionis et al. |
| 5,572,438 A | | 11/1996 | Ehlers et al. |
| 5,637,930 A | | 6/1997 | Rowen et al. |
| 5,770,926 A | | 6/1998 | Choi et al. |
| 5,818,128 A | | 10/1998 | Hoffman et al. |
| 5,822,012 A | | 10/1998 | Jeon et al. |
| 5,872,429 A | | 2/1999 | Xia et al. |
| 5,905,442 A | | 5/1999 | Mosebrook et al. |
| 5,909,087 A | | 6/1999 | Bryde et al. |
| 5,927,603 A | * | 7/1999 | McNabb .................. 239/63 |
| 5,962,989 A | | 10/1999 | Baker |
| 5,982,103 A | | 11/1999 | Mosebrook et al. |
| 6,025,783 A | | 2/2000 | Steffens, Jr. |
| 6,044,062 A | | 3/2000 | Brownrigg et al. |
| 6,100,653 A | | 8/2000 | Lovell et al. |
| 6,108,614 A | * | 8/2000 | Lincoln et al. .................. 702/183 |
| 6,148,306 A | | 11/2000 | Seidl et al. |
| 6,169,377 B1 | | 1/2001 | Bryde et al. |
| 6,175,860 B1 | | 1/2001 | Gaucher |
| 6,184,622 B1 | | 2/2001 | Lovell et al. |
| 6,249,516 B1 | | 6/2001 | Brownrigg et al. |
| 6,252,358 B1 | | 6/2001 | Xydis et al. |
| 6,297,724 B1 | | 10/2001 | Bryans et al. |
| 6,300,727 B1 | | 10/2001 | Bryde et al. |
| 6,301,674 B1 | | 10/2001 | Saito et al. |
| 6,311,105 B1 | | 10/2001 | Budike |
| 6,388,399 B1 | | 5/2002 | Eckel et al. |
| 6,400,280 B1 | | 6/2002 | Osakabe |
| 6,504,266 B1 | | 1/2003 | Ervin |
| 6,510,369 B1 | | 1/2003 | Lacy |
| 6,535,859 B1 | | 3/2003 | Yablonowski |
| 6,548,967 B1 | | 4/2003 | Dowling et al. |
| 6,633,823 B2 | | 10/2003 | Bartone et al. |
| 6,640,142 B1 | | 10/2003 | Wong et al. |
| 6,676,831 B2 | | 1/2004 | Wolfe |
| 6,689,050 B1 | | 2/2004 | Beutter et al. |
| 6,700,334 B2 | | 3/2004 | Weng |
| 6,775,588 B1 | | 8/2004 | Peck |
| 6,803,728 B2 | | 10/2004 | Balasubramaniam |
| 6,891,838 B1 | | 5/2005 | Petite et al. |
| 6,904,385 B1 | | 6/2005 | Budike, Jr. |
| 6,914,395 B2 | | 7/2005 | Yamauchi et al. |
| 6,914,893 B2 | | 7/2005 | Petite |
| 6,927,546 B2 | | 8/2005 | Adamson et al. |
| 6,990,394 B2 | | 1/2006 | Pasternak |
| 7,006,768 B1 | | 2/2006 | Franklin |
| 7,039,532 B2 | | 5/2006 | Hunter |
| 7,042,170 B2 | | 5/2006 | Vakil et al. |
| 7,045,968 B1 | | 5/2006 | Bierman et al. |
| 7,054,271 B2 | | 5/2006 | Brownrigg et al. |
| 7,079,808 B2 | | 7/2006 | Striemer |
| 7,103,511 B2 | | 9/2006 | Petite |
| 7,167,777 B2 | | 1/2007 | Budike, Jr. |
| 7,199,530 B2 | | 4/2007 | Vakil et al. |
| 7,202,613 B2 | | 4/2007 | Morgan et al. |
| 7,221,110 B2 | | 5/2007 | Sears et al. |
| 7,233,080 B2 | | 6/2007 | Garnault et al. |
| 7,263,073 B2 | | 8/2007 | Petite et al. |
| 7,274,975 B2 | | 9/2007 | Miller |
| 7,307,389 B2 | | 12/2007 | Vakil et al. |
| 7,307,542 B1 | | 12/2007 | Chandler et al. |
| 7,333,880 B2 | | 2/2008 | Brewster et al. |
| 7,339,466 B2 | | 3/2008 | Mansfield et al. |
| 7,346,433 B2 | | 3/2008 | Budike |
| 7,349,766 B2 | | 3/2008 | Rodgers |
| 7,352,972 B2 | | 4/2008 | Franklin |
| 7,354,175 B2 | | 4/2008 | Culbert et al. |
| 7,356,308 B2 | | 4/2008 | Hamada et al. |
| 7,369,060 B2 | | 5/2008 | Veskovic et al. |
| 7,400,226 B2 | | 7/2008 | Barrieau et al. |
| 7,417,556 B2 | | 8/2008 | Ling |
| 7,432,803 B2 | | 10/2008 | Fails et al. |
| 7,446,671 B2 | | 11/2008 | Giannopoulos et al. |
| 7,490,957 B2 | | 2/2009 | Leong et al. |
| 7,491,111 B2 | | 2/2009 | Ghaly |
| 7,528,503 B2 | | 5/2009 | Rognli et al. |
| 7,550,931 B2 | | 6/2009 | Lys et al. |
| 7,561,977 B2 | | 7/2009 | Horst et al. |
| 7,565,227 B2 | | 7/2009 | Richard et al. |
| 7,571,063 B2 | | 8/2009 | Howell et al. |
| 7,599,764 B2 | | 10/2009 | Matsuura et al. |
| 7,606,639 B2 | | 10/2009 | Miyaji |
| 7,623,042 B2 | | 11/2009 | Huizenga |
| 7,650,425 B2 | | 1/2010 | Davis et al. |
| 7,659,674 B2 | | 2/2010 | Mueller et al. |
| 7,677,753 B1 | | 3/2010 | Wills |
| 7,697,927 B1 | | 4/2010 | Owens |
| 7,706,928 B1 | | 4/2010 | Howell et al. |
| 7,719,440 B2 | | 5/2010 | Delp et al. |
| 7,755,505 B2 | | 7/2010 | Johnson et al. |
| 7,760,068 B2 | | 7/2010 | Hatemata et al. |
| 7,783,188 B2 | | 8/2010 | Clark |
| 7,812,543 B2 | | 10/2010 | Budike, Jr. |
| 7,839,017 B2 | | 11/2010 | Huizenga et al. |
| 7,843,353 B2 | | 11/2010 | Pan et al. |
| 7,860,495 B2 | | 12/2010 | McFarland |
| 7,880,394 B2 | | 2/2011 | Sibalich et al. |
| 7,884,732 B2 | | 2/2011 | Huizenga |
| 7,889,051 B1 | | 2/2011 | Billig et al. |
| 7,902,759 B2 | | 3/2011 | Newman, Jr. |
| 7,925,384 B2 | | 4/2011 | Huizenga |
| 8,033,686 B2 | | 10/2011 | Recker et al. |
| 8,214,061 B2 | | 7/2012 | Westrick, Jr. et al. |
| 8,275,471 B2 | | 9/2012 | Huizenga et al. |
| 8,344,665 B2 | | 1/2013 | Verfuerth et al. |
| 8,364,325 B2 | | 1/2013 | Huizenga et al. |
| 8,588,830 B2 | | 11/2013 | Myer et al. |
| 8,755,915 B2 | | 6/2014 | Huizenga et al. |
| 2001/0015409 A1 | * | 8/2001 | Mahler et al. .................. 250/342 |
| 2001/0025349 A1 | | 9/2001 | Sharood et al. |
| 2002/0009978 A1 | * | 1/2002 | Dukach et al. .................. 455/99 |
| 2002/0043938 A1 | | 4/2002 | Lys |
| 2003/0020595 A1 | | 1/2003 | Wacyk |
| 2003/0209999 A1 | | 11/2003 | Hui et al. |
| 2004/0002792 A1 | | 1/2004 | Hoffknecht |
| 2004/0051467 A1 | | 3/2004 | Balasubramaniam |
| 2004/0100394 A1 | | 5/2004 | Hitt |
| 2004/0153207 A1 | | 8/2004 | Peck |
| 2005/0043862 A1 | | 2/2005 | Brickfield et al. |
| 2005/0090915 A1 | | 4/2005 | Geiwitz |
| 2005/0234600 A1 | | 10/2005 | Boucher et al. |
| 2006/0044152 A1 | | 3/2006 | Wang |
| 2006/0142900 A1 | | 6/2006 | Rothman et al. |
| 2006/0161270 A1 | | 7/2006 | Luskin et al. |
| 2006/0215345 A1 | | 9/2006 | Huizenga |
| 2006/0244624 A1 | | 11/2006 | Wang et al. |
| 2006/0291136 A1 | | 12/2006 | Okishima |
| 2007/0005195 A1 | | 1/2007 | Pasquale et al. |
| 2007/0085700 A1 | | 4/2007 | Walters et al. |
| 2007/0090960 A1 | | 4/2007 | Miki |
| 2007/0229250 A1 | * | 10/2007 | Recker et al. .................. 340/531 |
| 2007/0271006 A1 | | 11/2007 | Golden et al. |
| 2007/0273307 A1 | | 11/2007 | Westrick et al. |
| 2007/0276547 A1 | | 11/2007 | Miller |
| 2007/0291483 A1 | | 12/2007 | Lys |
| 2008/0071391 A1 | | 3/2008 | Busby et al. |
| 2008/0133065 A1 | | 6/2008 | Cannon et al. |
| 2008/0167756 A1 | | 7/2008 | Golden et al. |
| 2008/0242314 A1 | | 10/2008 | McFarland |
| 2008/0258633 A1 | | 10/2008 | Voysey |
| 2008/0281473 A1 | | 11/2008 | Pitt |
| 2009/0018706 A1 | | 1/2009 | Wittner |
| 2009/0026966 A1 | | 1/2009 | Budde et al. |

(56) References Cited

U.S. PATENT DOCUMENTS

| | | |
|---|---|---|
| 2009/0045941 A1 | 2/2009 | Cooper |
| 2009/0048691 A1 | 2/2009 | Donaldson |
| 2009/0055032 A1 | 2/2009 | Rodgers |
| 2009/0058193 A1* | 3/2009 | Reid et al. ............ 307/116 |
| 2009/0063257 A1 | 3/2009 | Zak et al. |
| 2009/0066473 A1 | 3/2009 | Simons |
| 2009/0072945 A1 | 3/2009 | Pan et al. |
| 2009/0132070 A1 | 5/2009 | Ebrom et al. |
| 2009/0198384 A1 | 8/2009 | Ahn |
| 2009/0218951 A1 | 9/2009 | Weaver |
| 2009/0240381 A1 | 9/2009 | Lane |
| 2009/0243517 A1 | 10/2009 | Verfuerth et al. |
| 2009/0248217 A1 | 10/2009 | Verfuerth et al. |
| 2009/0261735 A1 | 10/2009 | Sibalich et al. |
| 2009/0262189 A1 | 10/2009 | Marman |
| 2009/0267540 A1 | 10/2009 | Chemel et al. |
| 2009/0278472 A1 | 11/2009 | Mills et al. |
| 2009/0278934 A1* | 11/2009 | Ecker et al. ............ 348/152 |
| 2009/0292402 A1 | 11/2009 | Cruickshank |
| 2009/0292403 A1 | 11/2009 | Howell et al. |
| 2009/0299527 A1 | 12/2009 | Huizenga et al. |
| 2010/0039240 A1 | 2/2010 | Rodriguez et al. |
| 2010/0052939 A1 | 3/2010 | Liang |
| 2010/0066267 A1 | 3/2010 | Meyer |
| 2010/0114340 A1 | 5/2010 | Huizenga et al. |
| 2010/0134019 A1 | 6/2010 | Berhorst |
| 2010/0134051 A1 | 6/2010 | Huizenga et al. |
| 2010/0141153 A1* | 6/2010 | Recker et al. ............ 315/149 |
| 2010/0164386 A1 | 7/2010 | You |
| 2010/0179670 A1 | 7/2010 | Forbes, Jr. et al. |
| 2010/0185339 A1 | 7/2010 | Huizenga et al. |
| 2010/0191388 A1 | 7/2010 | Huizenga et al. |
| 2010/0201203 A1 | 8/2010 | Schatz et al. |
| 2010/0204847 A1 | 8/2010 | Leete, III et al. |
| 2010/0207548 A1 | 8/2010 | Lott |
| 2010/0237783 A1 | 9/2010 | Dupre et al. |
| 2010/0262296 A1 | 10/2010 | Davis et al. |
| 2010/0265100 A1 | 10/2010 | Jalbout et al. |
| 2010/0327766 A1 | 12/2010 | Recker et al. |
| 2011/0006877 A1 | 1/2011 | Franklin |
| 2011/0012541 A1 | 1/2011 | Finch |
| 2011/0043052 A1 | 2/2011 | Huizenga et al. |
| 2011/0101871 A1 | 5/2011 | Schenk et al. |
| 2011/0112702 A1 | 5/2011 | Huizenga et al. |
| 2011/0121654 A1 | 5/2011 | Recker et al. |
| 2011/0133655 A1 | 6/2011 | Recker et al. |
| 2011/0175533 A1 | 7/2011 | Holman et al. |
| 2012/0001548 A1 | 1/2012 | Recker et al. |
| 2012/0020060 A1 | 1/2012 | Myer et al. |
| 2012/0026726 A1 | 2/2012 | Recker et al. |
| 2012/0043889 A1 | 2/2012 | Recker et al. |
| 2012/0074843 A1 | 3/2012 | Recker et al. |
| 2012/0080944 A1 | 4/2012 | Recker et al. |
| 2012/0098432 A1 | 4/2012 | Recker et al. |
| 2012/0098439 A1 | 4/2012 | Recker et al. |
| 2012/0143383 A1 | 6/2012 | Cooperrider et al. |
| 2012/0330476 A1 | 12/2012 | Huizenga et al. |
| 2013/0033183 A1 | 2/2013 | Verfuerth et al. |
| 2013/0103201 A1 | 4/2013 | Huizenga et al. |
| 2013/0113291 A1 | 5/2013 | Recker et al. |
| 2013/0131882 A1 | 5/2013 | Verfuerth et al. |
| 2013/0147366 A1 | 6/2013 | Huizenga et al. |
| 2013/0193847 A1 | 8/2013 | Recker et al. |
| 2013/0285558 A1 | 10/2013 | Recker et al. |

OTHER PUBLICATIONS

Canovas, S. R., Chermont, M.G., and Cugnasaca, C.E., "Remote Monitoring and Actuation Based on LonWorks Technology," Jul. 2005, 2005 EFITA/WCCA Joint Congress on IT in Agriculture.

Gislason, D. and Gillman, T. "ZigBee Wireless Sensor Networks," Nov. 2004, Dr. Dobbs online journal, www.ddj.com/184405887.

Gutierrez, J.A., "On the Use of IEEE Std. 802, 15.4 to enable Wireless Sensor Networks in Building Automation," Dec. 2007, Int'l. Journal of Wireless Information Network, vol. 14, No. 4.

Kintner-Meyer, M. "Opportunities of Wireless Sensors and Controls for Building Operations," Aug.-Sep. 2005, Energy Engineering, vol. 102, No. 5, pp. 27-48.

Montegi, N., Piette, M., Kinney, S., and Herter, K., "Web-Based Energy Information Systems for Energy Management and Demand Response in Commercial Buildings," Apr. 2003, Lawrence Berkeley National Laboratory.

Park, H., Burke, J., and Srivastava, M., "Design and Implementation of a Wireless Sensor Network for Intelligent Light Control," Apr. 2007, IPSN 07.

Sandhu, J.S.S., Agogino, A.M., "Wireless Sensor Networks for Commercial Lighting Control: Decision Making with Multi-Agent Systems," Jul. 2004, Workshop on Sensor Networks.

Sandhu, J.S., Agogino, A.M., and Agogino, A.K., "Wireless Sensor Networks for Commercial Lighting Control: Decision Making with Multi-Agent Systems," 2004, American Association for Artificial Intelligence.

Sekinger, J., "Wireless Lighting Control Technology," Oct. 2005, Phillips NAESCO Midwest Regional Mtgs.

Singhvi, V., Krause, A., Guestrin, C., Garrett, J.H., Matthews, H.S. "Intelligent Light Control Usine Sensor Networks," Nov. 2005, SenSys 2005.

Teasdale, D., Rubinstein, F., Watson, D., and Purdy, S., "Annual Technical Progress Report: Adapting Wireless Technology to Lighting Control and Environmental Sensing," Oct. 2005, Dust Networks, Annual Technical Progress Report.

Wang, D., Arens, E., and Federspiel, C., "Opportunities to same energy and improve comfort by using wireless sensor networks in buildings," Oct. 2003, Proceedings of the third intl Conference for Enhanced Building Operations.

* cited by examiner

WIRELESS SENSOR

CROSS-REFERENCE TO RELATED APPLICATIONS

This application claims the priority benefit of U.S. provisional application No. 61/258,845 filed Nov. 6, 2009 and U.S. provisional application No. 61/258,841 filed Nov. 6, 2009, the disclosures of which are incorporated herein by reference.

This application is also related to U.S. patent application Ser. No. 12/156,621 filed Jun. 2, 2008, now U.S. Pat. No. 8,364,325, U.S. patent application Ser. No. 12/380,727 filed Mar. 2, 2009, now U.S. Pat. No. 7,839,017, U.S. patent application Ser. No. 12/613,970 filed Nov. 6, 2009, and U.S. patent application Ser. No. 12/912,717 filed Oct. 26, 2010, now U.S. Pat. No. 8,275,471, the disclosures of which are also incorporated herein by reference.

BACKGROUND OF THE INVENTION

1. Field of the Invention

The present invention generally involves sensors. More specifically, the present invention relates to wireless detection of area changes.

2. Description of Related Art

In recent years, a growing concern over environmental responsibility and viability has prompted various measures to reduce energy consumption and ensuing costs. In commercial and residential settings, one solution is the use of a sensor for detecting certain environmental conditions and initiating a adjustment of an electrical load device (i.e., electricity-consuming device) in response to the detected condition(s). For example, some building installations (e.g., offices) have installed occupancy sensors to detect motion in a given location. An occupancy sensor wired to a lighting fixture, for example, may detect movement or lack of movement in a particular room and cause the lighting fixture to turn on or off in response. Such sensor may initiate such response by communicating with an actuator or switch of the electrical load device.

Issues with such a scheme may include inflexibility and difficulty and expense associated with retrofitting for changing and/or growing installations. For example, a sensor may have to be rewired when electrical load devices are added, removed, or relocated and when user preferences change. Such situations may require rewiring and reconfiguration of sensor settings to reflect the new arrangement and requirements thereof.

Presently available sensors generally operate by transmitting a signal over a wired connection to an actuator (e.g., relay, power pack), which provides for control of an electrical load. Such presently available sensors are not configured for wireless communication. As such, those sensors are limited to certain types of signals, such as those indicating detection of motion, or lack thereof.

Another challenge for such sensors in a conventional lighting control system is that such sensors are usually mounted at an elevated position (e.g., ceiling, wall). As such, the sensor may be remote from various parts of a location. For example, in an office, it may be desirable to determine the light level around a work surface (i.e., desk). Because the sensor is mounted in an elevated position, the sensor may end up measuring reflected light from both the target surface, as well as from the surrounding environment. As such, the sensor reading is inaccurate, thereby possibly resulting in inappropriate responses.

Other issues may include inflexibility to changing requirements of the occupants. For example, an occupant may require different lighting response on weekdays than he/she does on weekends. Sensors that are not sensitive enough may not detect fine movements (e.g., typing at a desk), and sensors that are over-sensitive may detect movement outside a door or window, resulting in responses that inappropriate to the actual situation in an area.

There is therefore a need in the art for improved methods and systems for wireless sensing.

SUMMARY OF THE INVENTION

Embodiments of the present invention include systems and methods for wirelessly detecting area changes. Predetermined thresholds may be stored in memory. Each predetermined threshold is associated with a time of day, calendar day, and/or activity. The sensor may detect a change in the in the targeted area. The detected change is evaluated to determine an applicable threshold. Then it may be determined whether the detected change meets a predetermined threshold. If so, information regarding the change is wirelessly transmitted to an associated controller that controls light in the targeted area. The operation of the light may be controlled based on the wirelessly transmitted information.

Various embodiments may include methods for wirelessly detecting area changes. Such methods may include storing a plurality of predetermined thresholds associated with time of day, calendar day, and/or activity. Methods may further include detecting a change in an area targeted by the wireless sensor, determining an applicable predetermined threshold, determining that the detected change meets the applicable predetermined threshold, wirelessly transmitting information indicating that the detected change meets the predetermined threshold to an associated controller concerning the change in overall light. The associated controller may then control operation of an electrical load based on the transmitted information. The detected change may occur with respect to light (e.g., red-green-blue light) and/or occupancy.

Some embodiments include an apparatus for wirelessly detecting area changes. Such apparatuses may include a memory for storing one or more predetermined thresholds associated with time of day, calendar day, and/or activity, a sensor cell for detecting a change in a targeted area, and a processor for determining an applicable threshold and determining that the detected change meets the applicable threshold. Such apparatuses may further include a wireless interface for wirelessly transmitting information to an associated controller concerning the change in overall light. The associated controller may then control operation of an electrical load based on the transmitted information. The sensor cell may be either a sensor cell for detecting light (e.g., red-green-blue light) and/or a sensor cell for detecting occupancy (e.g., passive infrared).

Further embodiments may include non-transitory computer-readable storage media having embodied instructions executable by a processor for performing methods for wirelessly detecting area changes.

DETAILED DESCRIPTION

Embodiments of the present invention provide for wirelessly detecting area changes. Predetermined thresholds may be stored in memory. Each predetermined threshold is associated with a time of day, calendar day, and/or activity. The sensor may detect a change in the in the targeted area. The detected change is evaluated to determine an applicable threshold. Then it may be determined whether the detected change meets a predetermined threshold. If so, information regarding the change is wirelessly transmitted to an associated controller that controls light in the targeted area. The operation of the light may be controlled based on the wirelessly transmitted information.

Figure 1:
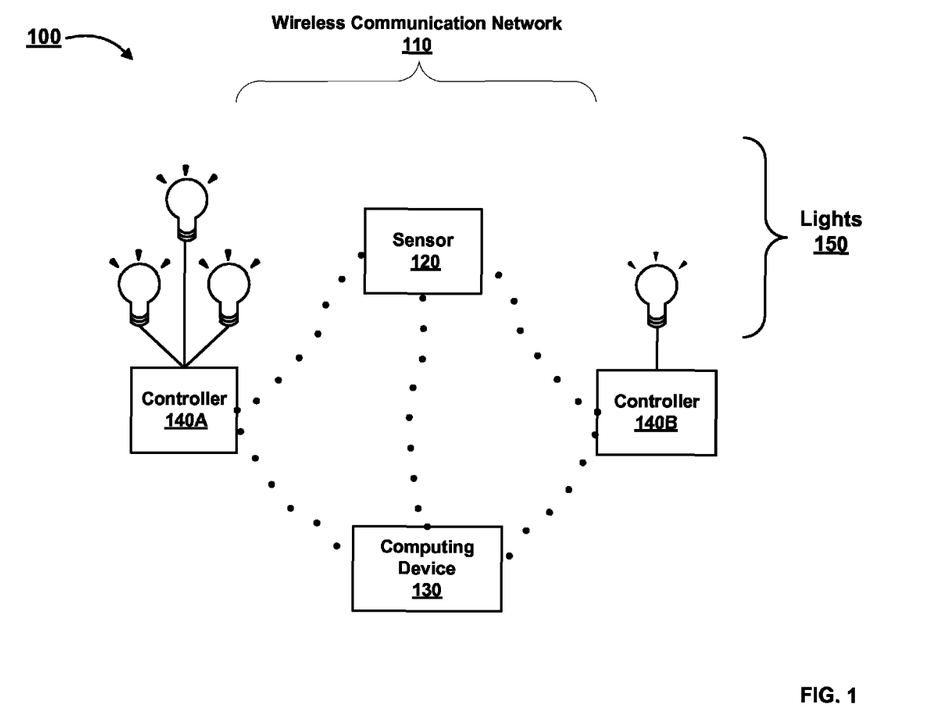
FIG. 1 illustrates an exemplary network environment in which a system for wirelessly detecting area changes may be implemented.

FIG. 1 illustrates an exemplary network environment 100 in which a system for wirelessly detecting area changes may be implemented. Communicating via a wireless communication network 110, devices in the network environment 100 include wireless sensor 120, computing device 130, and wireless controllers 140A-140B controlling lights 150.

Wireless communication network 110 may be inclusive of any local, proprietary network (e.g., an intranet), as well as any larger wide-area network. The communications network 110 may include a local area network (LAN), for example, which may be communicatively coupled to a wide area network (WAN) such as the Internet. The Internet is a broad network of interconnected computers and servers allowing for the transmission and exchange of Internet Protocol (IP) data between users connected through a network service provider. Examples of network service providers are the public switched telephone network, a cable service provider, a provider of digital subscriber line (DSL) services, or a satellite service provider. In some embodiments, the network environment 100 may be configured to transmit various electromagnetic waves, including, for example, radio signals. Examples of the communication network 110 may include IEEE 802.11 (Wi-Fi or Wireless LAN) networks, IEEE 802.16 (WiMAX) networks, IEEE 802.16c networks, and the like. Wireless Communications network 110 allows for communication between the various components of network environment 100. In some instances, communication network 110 may be a multi-hop network.

One of the devices in environment 100 is a wireless sensor 120 including one or more sensor cells. A wireless sensor may include various types of sensor cells for detecting various conditions, including occupancy (e.g., motion), photosensors, RGB sensors, passive infrared (PIR) sensors, or any combination of the foregoing. PIR sensors may be used, in some installations, to provide more detailed information concerning a targeted area. For example, information from a PIR may be used to establish a baseline with respect to an empty room and an individual. In some instances, such information may be used to determine when there are multiple people present in a room and generate an estimate as to how many people. Such information may also allow for targeted control of other types of facilities systems besides lighting (e.g., HVAC systems).

The inclusion of multiple sensors may also serve reduce power usage, based on intelligent determination as to when to activate each sensor. For example, not all the sensors have to be active at all times. Activation of a photosensor or RGB sensor, for example, may be activated upon detection of motion in a targeted area. Alternatively, a motion sensor may be activated only when it is dark. As such, the energy to power every sensor may not be continuously required. Such energy may be provided by a DC connection, battery, photovoltaic cell, or any combination.

The wireless sensor 120 may therefore be able to accurately measure light in a given targeted area (e.g., a desk or work surface, a room). In particular, such a wireless sensor 120 can independently detect and measure the red, green and blue (RGB) spectrums of light. Further, each wireless sensor 120 can then characterize common patterns of the three spectra to eliminate errors in calculating lighting levels in a given area. For example, a work surface may include different amounts of white paper, which may reflect light differently than the work surface does. As such, a sensor may be prone to error based on the variance in reflected light if no consideration is given to such factors.

Wireless sensor 120 can resolve such issues by storing information in memory regarding light signatures associated with various contexts (e.g., time of day). If there is a detected change in light levels, the wireless sensor 120 may first verify whether the detected change is actually a change in illuminance in the targeted area rather than a change due to, for example, more reflective white paper in the targeted area. In addition, the wireless sensor 120 may also consider whether the detected change in illuminance merits a response by comparing the change to predetermined thresholds. For example, a small change in illuminance may not necessarily require that an additional lamp/light be switched on or off. As such, there may be thresholds set by default, an administrator, or user, regarding what type of lighting change should result in a response. As such, in addition to its sensor cells, wireless sensor 120 may further include a memory and processor to store and make such determinations.

In various embodiments, a wireless sensor 120 can address and account for changes in reflectance vis-à-vis changes in amount of light. If the reflectance in the environment changes, then the light level sensor readings might increase even if the actual illuminance on the work surface does not. A common example may be observed when white papers are spread out on a brown conference table. For open-loop sensors, a similar situation may arise as a result of changes in ground reflectance (e.g., seasonal changes from green grass to brown grass to snow) or reflectances from unintended objects (e.g., windows, metallic window frames, automobiles). In wireless sensor 120, such changes in reflectance can be detected and identified based on measured changes in RGB light. As such, an exemplary wireless sensor 120 can recognize a signature of a color shift as a different condition than a change in work surface illuminance.

An exemplary wireless sensor 120 can also be configured to quantify the amount of artificial light vis-à-vis natural light (i.e., sunlight). Presently available sensors have difficulty accounting for two very different sources of light: natural light and artificial light. The amount of light reaching a sensor intended to measure illuminance at a given work surface may be different based on varying amounts of natural and artificial light. In the case of artificial lighting, error may be introduced based on reflectance from the work surface. With natural light, reflectance may be introduced from surfaces other than the work surface, including from lights interior and exterior to the area (e.g., light from a hallway or window). The light detected by a sensor at the targeted area will not be the same for equivalent amounts of natural light and artificial light. In other words, x lux of natural light is not equivalent to x lux of electric light.

An exemplary wireless sensor 120 addresses the problem by measuring RGB light to identify a color signature for natural light in the targeted area. The color signature may be determined based on several factors specific to the targeted area, including for example, spectral transmission of the glass windows in the area. Using such information, a wireless sensor 120 can calculate a percent of light provided by artificial light sources and a percent of light provided by natural light, as well as further calculate and quantify the contribution of natural and artificial light to illuminance of the targeted area.

In some embodiments, a wireless sensor 120 may perform an automated routine to identify a natural light signature when artificial lights are turned off. Under certain conditions, direct beam sunlight may enter into a targeted area (e.g., through a window). Direct beam sunlight may have a different spatial distribution than natural light under other conditions. To avoid overestimating the contribution of natural light to illuminance, a wireless sensor 120 may specifically characterize the signature of direct beam sunlight, as well as a signature of natural light under different conditions.

Being able to accurately determine illuminance allows for more customized control and concurrent reduction in power usage associated with artificial lights. For example, when the illuminance provided by natural light is sufficient, the artificial lights may be deactivated and only activated when natural light is no longer sufficient. Further, reduction in power usage related to artificial lights may be accomplished either by switching off or dimming.

Another type of condition that may be detected by wireless sensor 120 is occupancy of the targeted area. Such a sensor cell (e.g., passive infrared (PIR)) may operate to detect motion by human occupants having a body temperature different than the ambient temperature in an unoccupied targeted area. For example, an unoccupied room may normally have ambient temperatures ranging between 55 and 65 degrees Fahrenheit during an average spring day. As such, the wireless sensor 120 may recognize or be programmed to recognize that as a signature of an unoccupied room. When an occupant passes in front of the wireless sensor, however, the wireless sensor 120 can detect the higher body temperature of the occupant (e.g., 98 degrees Fahrenheit). As such, the detected presence of such higher temperatures can indicate occupancy of the targeted area. Such wireless sensors 120 may also be prone to error, however, where the purported occupant is merely passing by a window or door rather than entering the targeted area proper (e.g., a room).

Such a wireless sensor 120 can work with sensors intended for both open-loop and closed-loop control algorithms. Open-loop sensors are usually not intended to see the controlled light. For example, an open-loop sensor may be mounted to monitor an outside area because electric light extends to the building perimeter. Typically, this can involve mounting on a ceiling such that the sensor monitors an area outside of a window. In contrast, a closed-loop sensor usually monitors a controlled lighting area.

Some embodiments allow for fine-tuning of the wireless sensor 120 based on various factors, including time of day, calendar day, and/or activity. Sensitivity of the wireless sensor 120 refers to a trigger level (e.g., amount of detected occupants/motion, light) with respect to triggering a response from the sensor (e.g., to turn a lamp on/off). Delay refers to a time delay with respect to sending the response, for example, to an actuator associated with a lamp. A wireless sensor 120 may be programmed to have different sensitivity or delays based on specific circumstances. For example, sensitivity level may be programmed to be higher, for example, so that a worker would be provided with light during working hours. Alternatively, sensitivity of the sensor may be adjusted to be lower on weekends and holidays when workers are less likely to be in an office, so that movement of wind-blown trees outside a window does not trigger lights to turn on.

After a predetermined condition is detected in a targeted area by a sensor included in an exemplary wireless sensor, information concerning the detected condition is sent wirelessly to a controller associated with an electrical load. The controller may then control operation of a device associated with the electrical load based on the information from the wireless sensor. In contrast to many previously available sensors (e.g., that sends only binary data), a wireless sensor 120 can transmit much more information via radio, as well as respond in much more targeted ways. A wireless sensor can adjust time delays and sensitivity based on various situations.

Further, a wireless sensor can adjust sensitivity based on a breakdown on a targeted area. For example, a wireless sensor 120 can be programmed to be less sensitive to an area by the door to avoid turning lights on in response to passers-by, as well as more sensitive around a workspace where movements (i.e., typing) may be smaller. Some embodiments further provided for masking of certain areas. Not only may sensitivity be deadened around a door area, a user may wish to totally mask the door, such that a sensor is "blind" to movements outside the door. For example, a wireless sensor 120 may include a quad element PIR. The quad element PIR works by providing data for two pairs of sensor cells, B and B', and A and A' while the dual element only compares one pair of elements. When paired with an appropriate Fresnel lens, sensing could occur on one half of the sphere or primarily on one half of the sphere. As such, the sensitivity of the particular sensor cells may be adjusted based on the portion of the targeted area to which it is directed (e.g., a door opening into a hallway).

Such configuration as to delay, sensitivity, and masking may take place at startup (e.g., commissioning) or remotely through computing device 130. Using computing device 130, an installer, building administrator, or user may be able to adjust such configurations to the requirements of the targeted area. Computing device 130 may comprise any combination of computer hardware and software configured to receive and transmit information over wireless communication network 110, thereby communicating with wireless sensor 120 and controllers 140A-140B. Computing device 130 may be any type of desktop computer, laptop computer, handheld computer, server, etc. configured to communication over wireless communication network 110. If wireless communication network 110 is a multi-hop network, computing device 130 may be able broadcast a message to devices within a specified number of hops in the communications network 110.

The controller (e.g., 140A) may be embedded in a fixture, housed within a ballast, in a separate device, etc. As illustrated in FIG. 1, a controller 140 may be associated with one or more light fixtures. Described in further detail in co-pending U.S. patent application Ser. No. 12/156,621 which has incorporated herein by reference, the controller 140 can controls the operation of the device or devices (i.e., lights) based on various types of signal information, including signal information sent over the communication network 110 from wireless sensor 120 and/or computing device 130. The controller 140 may be associated with one or more fixtures of a facilities system. In the embodiment illustrated in FIG. 1, such fixtures are lights 150. For example, the controller 140A is associated with three lights 150, while controller 140B is associated with one light 150. While the description refers to lights 150, controller 140 may control operation of any kind of electric fixture or appliance.

Where there are multiple controllers 140 controlling different sets of fixtures in a targeted area, the information sent by wireless sensor 120 to each controller may be different. For example, wireless sensor 120 may have a higher sensitivity (e.g., a lower threshold) associated with the portion of the targeted area where the lights 150 controlled by controller 140A are located. In response to a detected change that triggers that threshold (but does not trigger any other thresholds associated with other portions of the targeted area), the lights 150 controlled by controller 140A may be switched on while the lights 150 controlled by controller 140B are not.

Figure 2:
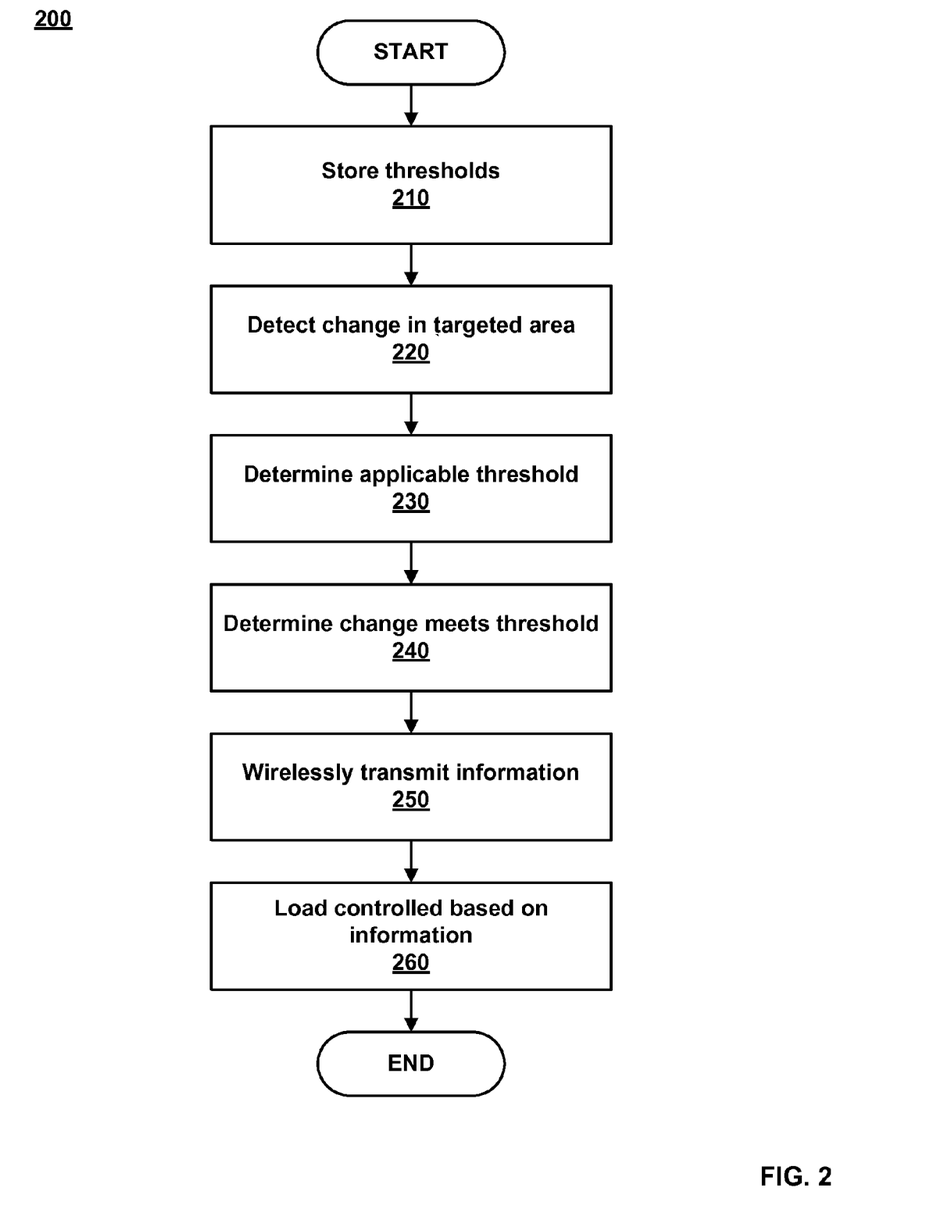
FIG. 2 is a flowchart illustrating an exemplary method for wirelessly detecting area changes.

FIG. 2 is a flowchart illustrating an exemplary method 200 for wirelessly detecting area changes. In the method 200, a plurality of thresholds are stored in memory, a change is detected in the targeted area, an applicable threshold is determined, and it is determined that the detected change meets the applicable threshold. Information indicating that the detected change meets the applicable threshold is wirelessly transmitted to an associated controller, which controls an electric load based on the transmitted information.

In step 210, various thresholds are stored in memory. Each threshold may relate to a type of condition detectable by wireless sensor 120, as well as at least one factor indicating when the threshold applies. Such factors may include, for example, time of day, calendar day (e.g., weekday or weekend, holiday), or activity. For example, one threshold may indicate that on weekday afternoons, the threshold can be highly sensitive. As such, detecting a lack of natural light may allow for artificial lights to be switched on to compensate. In an office, for example, occupants are still likely to be working and in need of a certain level of light to perform their work. In contrast, on weekends, occupants are unlikely to be in the office. As such, the threshold may be lower so that non-occupant movement (e.g., wind-blown trees outside a window) does not result in wasteful activation of lighting. The thresholds may be set based on default settings or be created/customized based on the particular needs of the facility, building, business, occupant, etc.

In step 220, a change is detected in the targeted area. The variety of sensors that may be deployed, as well as the conditions that are detectable by the same, are described above. In some cases, the wireless sensor 120 may be programmed with a baseline, either upon commissioning or later based on updated circumstances (e.g., by remote computing device 130). Such a baseline may indicate the normal range of conditions in the targeted area. In comparison to such a baseline, some type of change (e.g., light, occupancy, motion) in the targeted area may be detected.

In step 230, an applicable threshold is determined. The factors associated with the stored thresholds may be evaluated to determine which threshold is appropriate to the situation in which the change was detected. For example, a change in RGB light may have been detected on a weekday morning. As such, it is determined which of the stored thresholds are applicable to RGB light changes on weekday mornings.

In step 240, it is determined whether the detected change meets the applicable threshold. It would be inefficient to activate or deactivate fixtures (e.g., lights 150) in response to small changes. A minor decrease in natural light due to a passing cloud, for example, should not affect an office occupant's ability to work. As such, the detected change must be significant enough to merit a response in terms of activating or deactivating electric fixtures. In some circumstances, multiple thresholds may apply. For example, an occupancy sensor may detect a high probability that occupants have entered the targeted area. Meeting the occupancy threshold may further trigger light sensors to activate and determine whether the light level meets a light threshold.

In step 250, information regarding the determination is wirelessly transmitted to an associated controller 140. Specifically, such information may indicate that the detected change meets a certain applicable threshold. In response to such information, the controller 140 (e.g., associated with the portion of the targeted area for which the detected change is relevant) may control the operation of one or lights 150. For example, where the information indicates a significant decrease of light in particular quadrant of a room, the wireless sensor 120 may send such information to a controller 140 controlling lights 150 located in that quadrant.

In step 260, an electric load is controlled based on the wirelessly transmitted information. Referring to the example above, the controller 140 in the particular quadrant may receive such information from the wireless sensor 120. In response, such controller 140 may then switch on lights 150 or increase the brightness of such lights 150 if they were previously dimmed.

In some embodiments, it may be possible to view and generate reports concerning recent commands transmitted from the wireless sensor 120, configuration information, operation information, and times and dates of certain events. Such events may include triggering events (e.g., start and finish) within a period of time, sensor heartbeat messages, percentage of remaining battery life, and ambient temperature at intervals. Dates and times may be correlated with the sensor events. It may also be useful to view reported temperatures to evaluate and adjust settings in response to situations where the wireless sensor 120 did not detect changes (e.g., entering occupants) due to extreme temperatures (e.g., too high or too low) in the targeted area.

The terms "computer-readable storage medium" and "computer-readable storage media" as used herein refer to a medium or media that participates in providing instructions to a CPU for execution. Such media may take many forms including, but not limited to, non-volatile and volatile media. Non-volatile media include, for example, optical or magnetic disks, such as a fixed disk. Volatile media include dynamic memory, such as system RAM. Common forms of computer-readable storage media include, for example, a floppy disk, a flexible disk, a hard disk, magnetic tape, any other magnetic medium, a CD-ROM disk, digital video disk (DVD), any other optical medium, punch cards, paper tape, any other physical medium with patterns of marks or holes, a RAM, a PROM, an EPROM, a FLASHEPROM, any other memory chip or cartridge.

While the present invention has been described in connection with a series of preferred embodiments, these descriptions are not intended to limit the scope of the invention to the particular forms set forth herein. The above description is illustrative and not restrictive. Many variations of the invention will become apparent to those of skill in the art upon review of this disclosure. The scope of the invention should, therefore, be determined not with reference to the above description, but instead should be determined with reference to the appended claims along with their full scope of equivalents. The present descriptions are intended to cover such alternatives, modifications, and equivalents as may be included within the spirit and scope of the invention as defined by the appended claims and otherwise appreciated by one of ordinary skill in the art.

What is claimed is:

1. A method of wirelessly detecting area changes, the method comprising:
   storing a plurality of predetermined thresholds in a memory, the plurality of predetermined thresholds comprising time of day, calendar day, and activity, wherein the activity is related to an estimated number of occupants within an area targeted by a wireless sensor;

detecting a change in the area targeted by the wireless sensor;
executing instructions stored in the memory, wherein execution of the instructions by a processor:
  masks a portion of the targeted area by modifying a sensitivity threshold associated with the portion of the targeted area, wherein the masked portion of the targeted area is associated with a different sensitivity level than an unmasked portion of the targeted area;
  determines at least two applicable thresholds out of the plurality of predetermined thresholds stored in the memory, wherein one of the at least two applicable thresholds includes the activity; and
  determines that the detected change meets the at least two applicable thresholds;
wirelessly transmitting information indicating that the detected change meets the at least two thresholds to an associated controller, wherein the associated controller controls power usage of a device associated with the unmasked portion of the area targeted by the wireless sensor, based on the transmitted information; and
detecting a change in levels of red-green-blue light in the targeted area, wherein the determination that the detected change meets the two applicable thresholds out of the plurality of predetermined thresholds include:
  verifying that the detected change in the levels of red-green-blue light is associated with a change in illuminance; and
  determining that the change in illuminance meets the two applicable thresholds.

2. The method of claim 1, wherein the detected change further includes a change in occupancy of the unmasked portion of the targeted area as detected by passive infrared sensor cell.

3. The method of claim 2, wherein the control of the power usage results in a reduced lighting level for a predetermined time period and further comprising:
  determining whether the unmasked portion of the targeted area is occupied during the predetermined time period, wherein the duration of the predetermined time period is increased or decreased based on specified conditions; and
  transmitting the determination whether the unmasked portion of the targeted area is occupied during the predetermined time period to the associated controller.

4. The method of claim 2, wherein the wirelessly transmitted information further includes a probability of occupancy and wherein the probability of occupancy is evaluated to determine a priority for shedding in a demand response situation.

5. The method of claim 2, wherein the detected change in occupancy further includes a change from no occupants to one or more occupants and wherein wirelessly transmitting the information results in one or more lights being switched on.

6. The method of claim 2, wherein the detected change in occupancy further includes a change from one or more occupants to no occupants and wherein wirelessly transmitting the information results in one or more lights being switched off.

7. An apparatus for wirelessly detecting area changes, the apparatus comprising:
  a memory configured to store one or more predetermined thresholds stored in the memory, the predetermined thresholds comprising time of day, calendar day, and activity, wherein the activity is related to an estimated number of occupants within an area targeted by a wireless sensor;
  a sensor cell configured to detect a change in a targeted area;
  a processor configured to execute instructions stored in the memory to:
    mask a portion of the targeted area by modifying a sensitivity threshold associated with the portion of the targeted area, wherein the masked portion of the targeted area is associated with a different sensitivity level than an unmasked portion of the targeted area;
    determine at least two applicable thresholds out of the plurality of predetermined thresholds stored in the memory based on the detected change, wherein one of the at least two applicable thresholds includes the activity; and determine that the detected change meets the at least two applicable thresholds; and
  an interface configured to wirelessly transmit information indicating that the detected change meets the at least two applicable thresholds to an associated controller concerning the change in overall power usage of a light for the unmasked portion of the targeted area by the wireless sensor, wherein the associated controller controls power usage of the light, based on the transmitted information; and detect a change in levels of red-green-blue light in the targeted area,
  wherein the determination that the detected change meets a predetermined threshold includes: verifying that the detected change in the levels of red-green-blue light is associated with a change in illuminance, and determining that the change in illuminance meets the at least two applicable thresholds.

8. The apparatus of claim 7, wherein the sensor cell includes a passive infrared sensor for further detecting a change in occupancy of the targeted area.

9. The apparatus of claim 8, further comprising a timekeeper, wherein the control of the power usage results in a reduced lighting level for a predetermined time period indicated by the timekeeper and wherein the sensor cell is further configured to:
  determine whether the targeted area is occupied during the predetermined time period; and
  transmit the determination to the associated controller.

10. The apparatus of claim 9, wherein the duration of the predetermined time period is automatically increased or decreased based on preset conditions.

11. The apparatus of claim 7, further comprising one or more additional sensor cells, wherein each sensor cell is associated with a sensitivity threshold and a portion of the unmasked portion of the targeted area.

12. The apparatus of claim 7, wherein the wirelessly transmitted information includes a probability of occupancy and wherein the probability of occupancy is evaluated to determine a priority for shedding in a demand response situation.

13. A non-transitory computer-readable storage medium, having embodied thereon a program, the program being executable by a processor to perform a method for wirelessly detecting area changes, the method comprising:
  storing a plurality of predetermined thresholds, the predetermined thresholds comprising of time of day, calendar day, and activity, wherein the activity is related to an estimated number of occupants within an area targeted by a wireless sensor;
  masking a portion of the targeted area by modifying a sensitivity threshold associated with the portion of the targeted area, wherein the masked portion of the targeted area is associated with a different sensitivity level than an unmasked portion of the targeted area;

detecting a change in the area targeted by the wireless sensor;

determining at least two applicable thresholds out of the plurality of predetermined thresholds based on the detected change, wherein one of the at least two applicable thresholds includes the activity;

determining that the detected change meets the at least two applicable thresholds;

wirelessly transmitting information indicating that the detected change meets the at least two thresholds to an associated controller concerning the change in an overall power usage of a light for the unmasked portion of the targeted area by the wireless sensor, wherein the associated controller controls the power usage based on the transmitted information; and detecting a change in levels of red-green-blue light in the unmasked portion of the targeted area that meets the at least two applicable thresholds includes:
  verifying that the detected change in the levels of red-green-blue light is associated with a change in illuminance; and
  determining that the change in illuminance meets the at least two applicable thresholds.

\* \* \* \* \*